United States Patent
Rincoe

(10) Patent No.: US 6,436,149 B1
(45) Date of Patent: *Aug. 20, 2002

(54) ARTIFICIAL ANKLE JOINT AND PROSTHETIC DEVICES FORMED THEREWITH

(76) Inventor: Richard G. Rincoe, 49 S. Holman Way, Golden, CO (US) 80401

(*) Notice: Subject to any disclaimer, the term of this patent is extended or adjusted under 35 U.S.C. 154(b) by 0 days.

This patent is subject to a terminal disclaimer.

(21) Appl. No.: 08/999,693

(22) Filed: Aug. 27, 1996

Related U.S. Application Data

(63) Continuation-in-part of application No. 08/315,985, filed on Sep. 30, 1994.

(51) Int. Cl.$^7$ .................................................. A61F 2/66
(52) U.S. Cl. .......................................... 623/47; 623/52
(58) Field of Search ........................... 623/47–52, 53, 623/40–42

(56) References Cited

U.S. PATENT DOCUMENTS

| | | | | |
|---|---|---|---|---|
| 995,817 A | * | 6/1911 | Vanorman | 623/49 |
| 5,443,522 A | * | 8/1995 | Hiemisch | 623/49 |
| 5,728,175 A | * | 3/1998 | Rincoe | 623/49 |

FOREIGN PATENT DOCUMENTS

| | | | | |
|---|---|---|---|---|
| CA | 180745 | * | 12/1917 | 623/52 |
| DE | 299321 | * | 7/1917 | 623/53 |
| DE | 1 211 354 | * | 2/1966 | 623/49 |
| DE | 1 284 035 | * | 11/1968 | 623/50 |
| GB | 852362 | * | 10/1960 | 623/53 |

* cited by examiner

Primary Examiner—David H. Willse
(74) Attorney, Agent, or Firm—Timothy J. Martin; Michael R. Henson; Mark H. Weygandt

(57) ABSTRACT

A prosthetic device is provided having a proximal end portion adapted to be secured to an amputee and a distal foot structure. The improvement comprises a pivoting ankle joint disposed between the proximal end portion and the foot structure. This ankle joint includes a matable socket and head assembly interconnecting the proximal end portion and the foot structure for relative movement about a pivot axis between first and second positions. A spring element operates to resiliently bias the socket and head into the first pivot position. A load-sensitive locking mechanism operates, upon the existence of a triggering load which exceeds a predetermined threshold magnitude, to cause the socket and head assembly to lock at a selected locking position, thereby preventing relative pivotal movement. In the absence of the triggering load, relative pivotal movement of the socket and head assembly between the first and second positions is permitted.

19 Claims, 8 Drawing Sheets

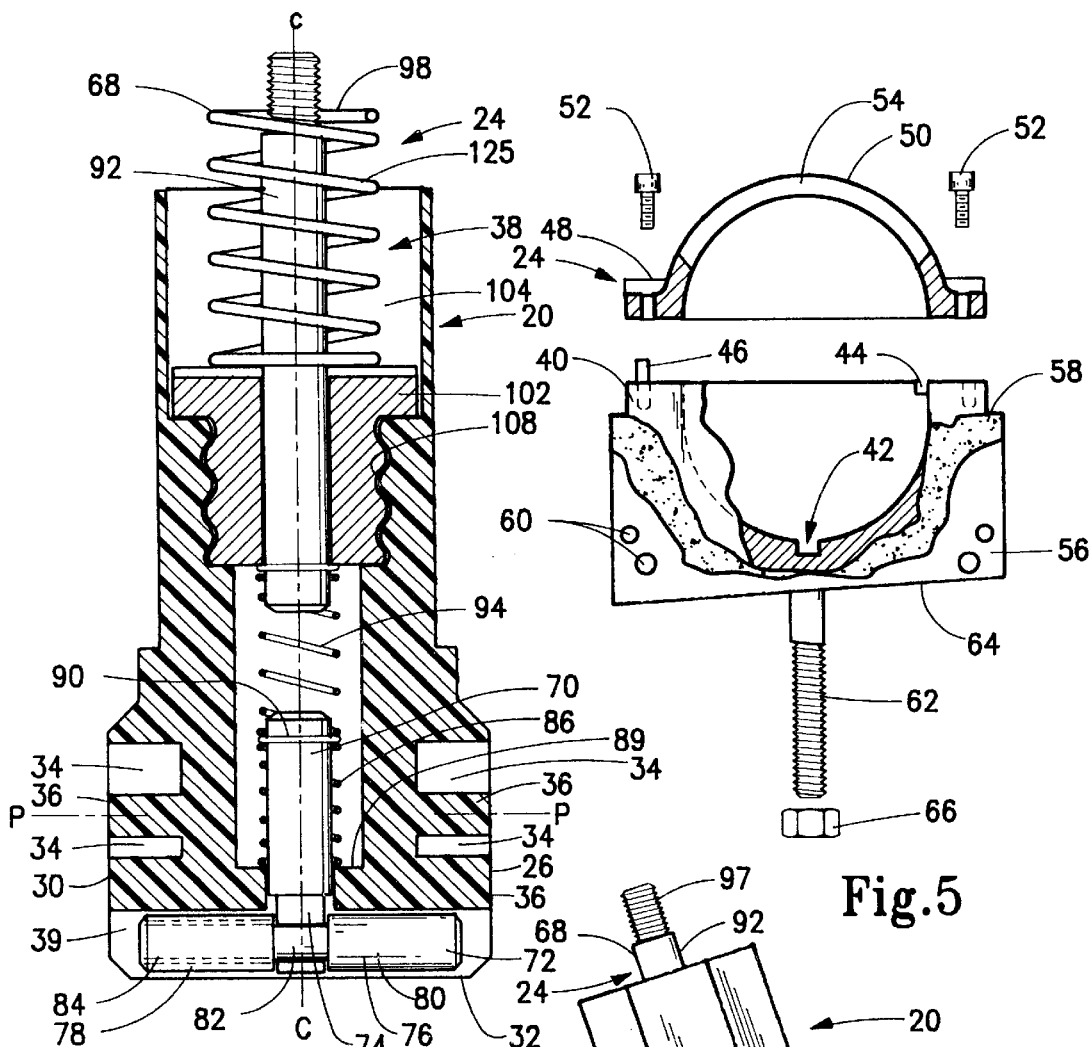
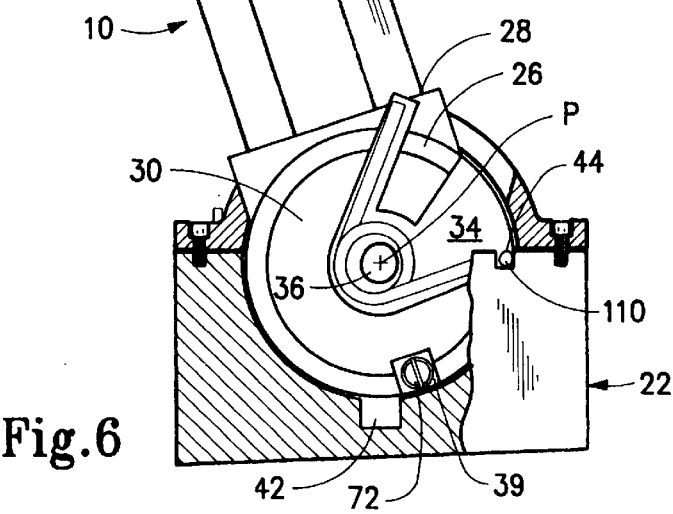
Fig.4
Fig.5
Fig.6

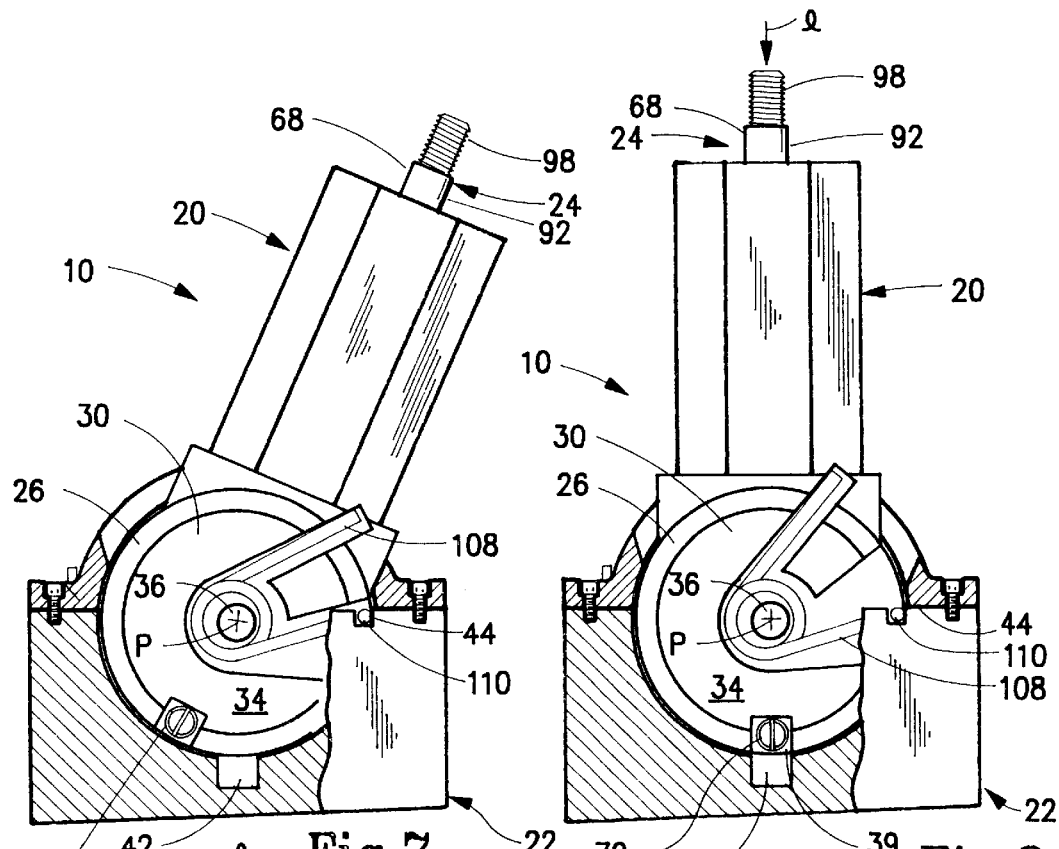
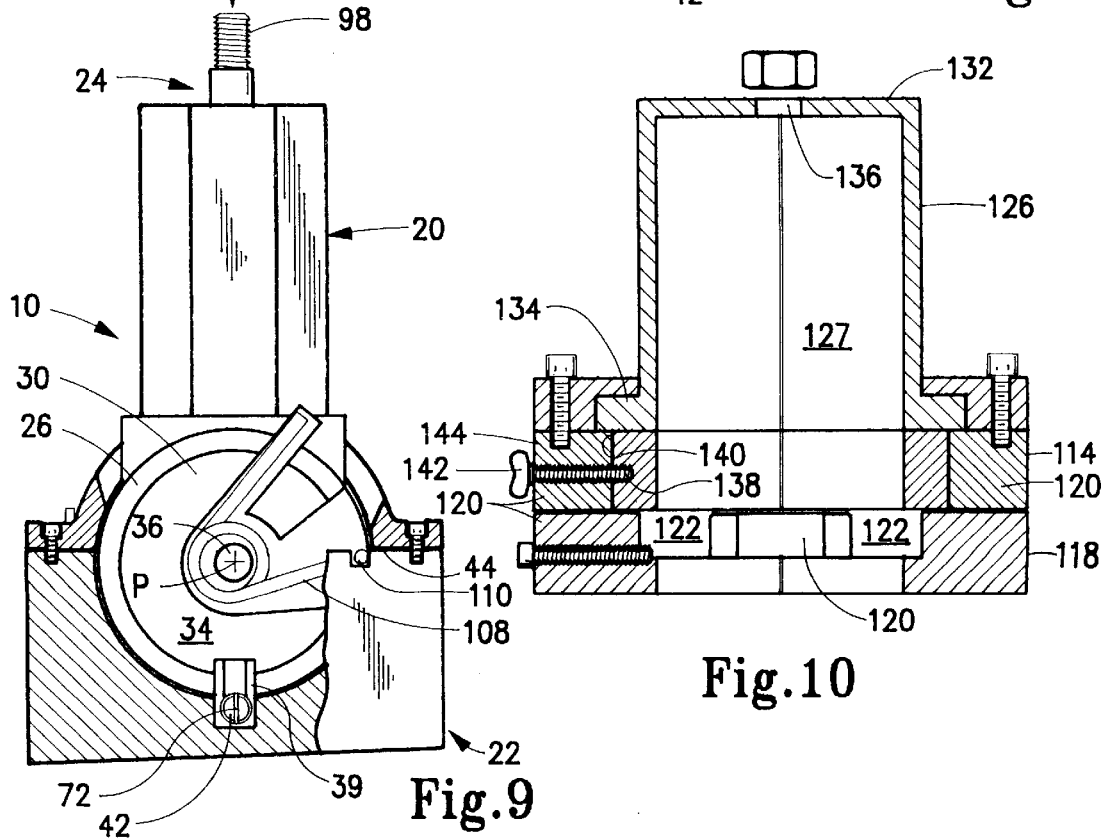

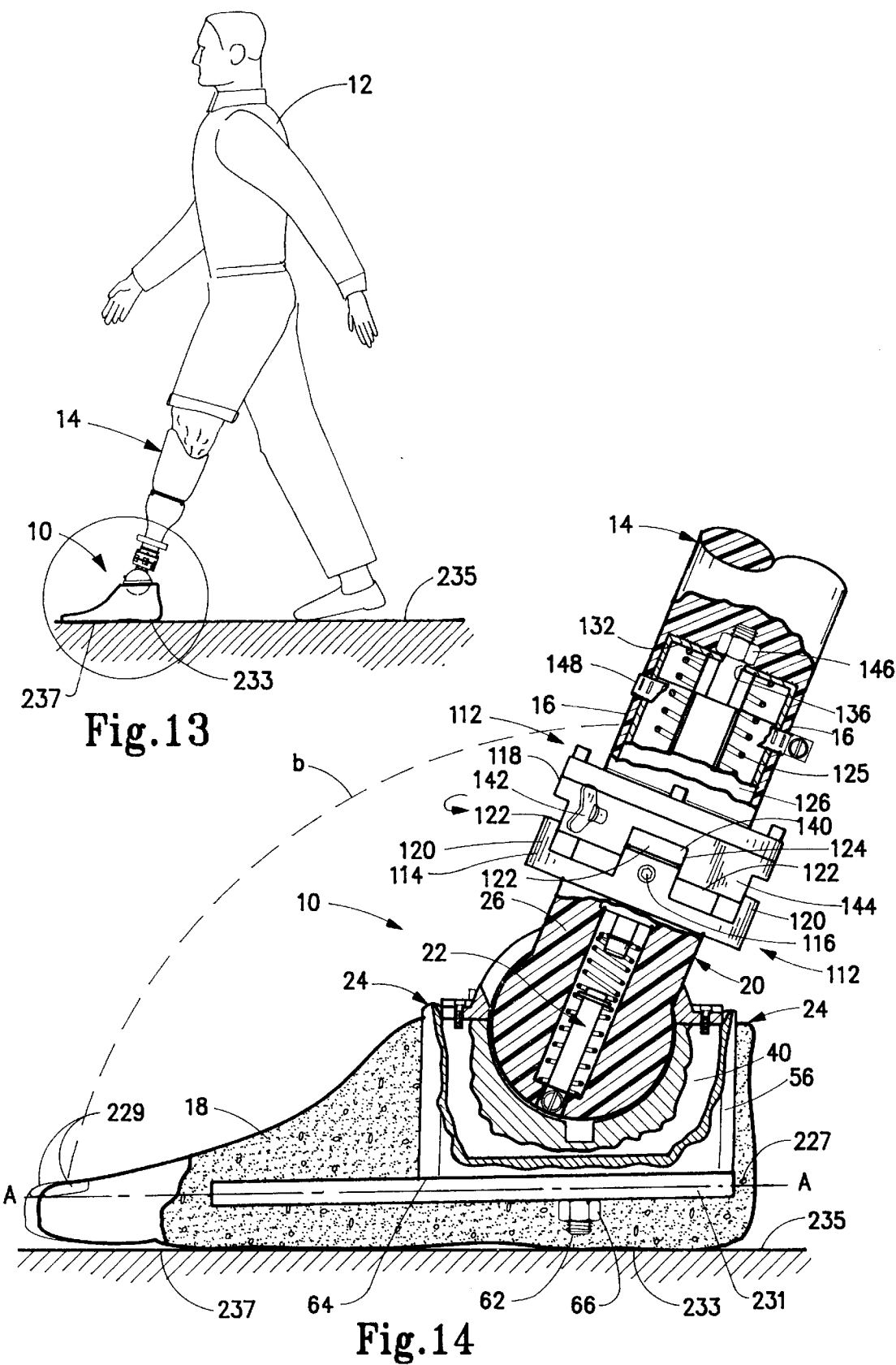

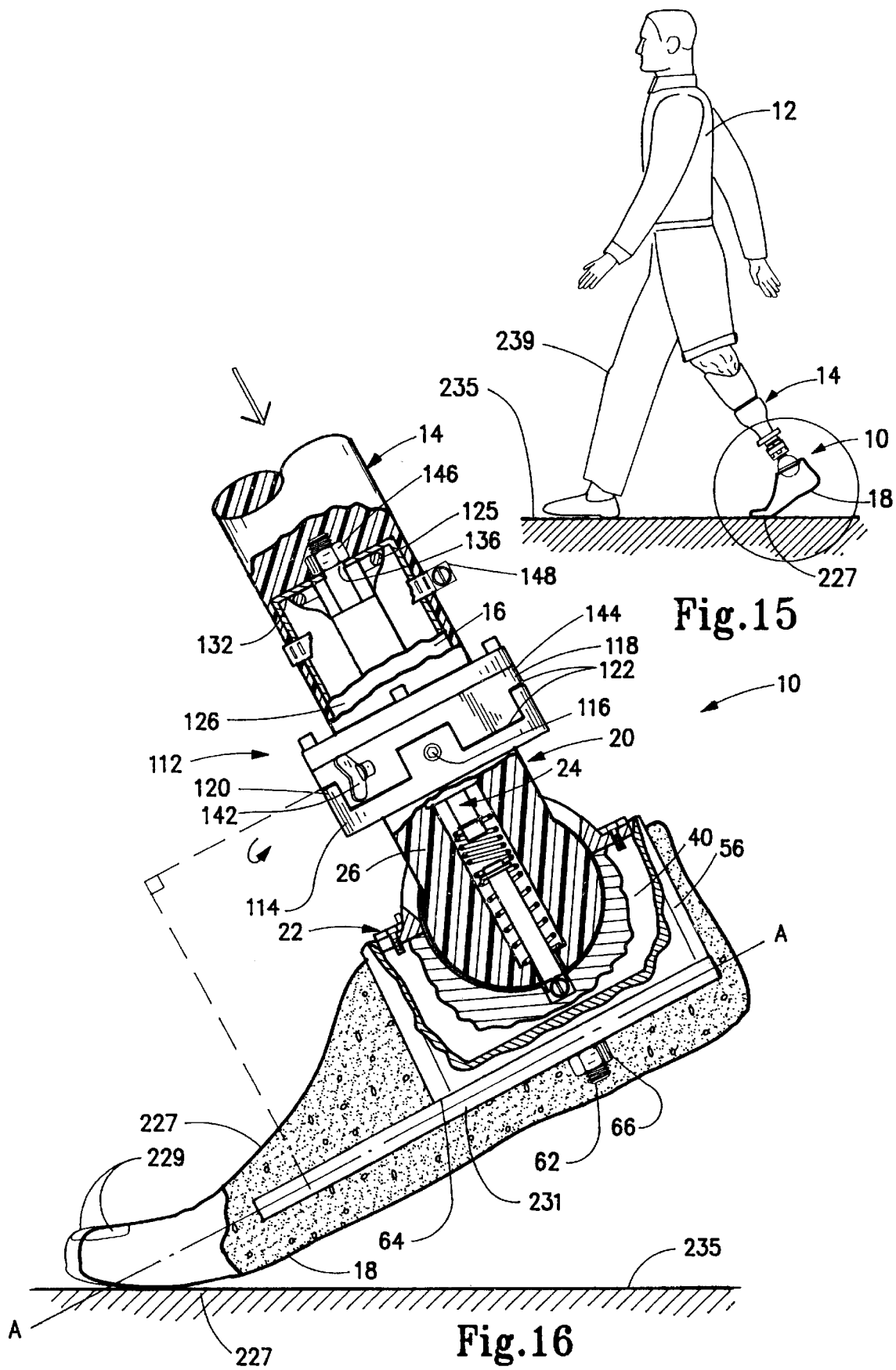

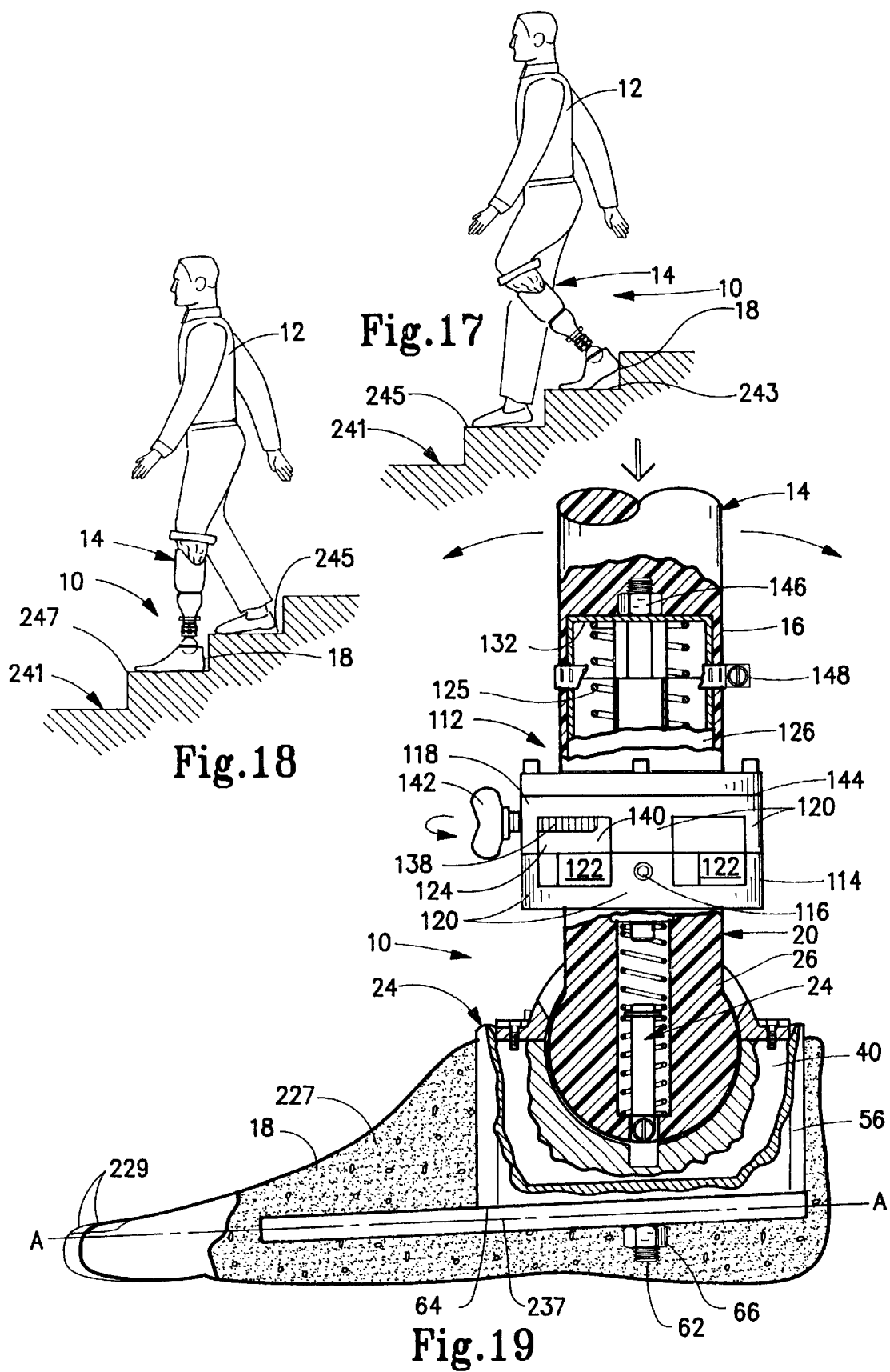

ARTIFICIAL ANKLE JOINT AND PROSTHETIC DEVICES FORMED THEREWITH

The present application is a continuation-in-part of my U.S. patent application Ser. No. 08/315,985, filed Sep. 30, 1994 and entitled ARTIFICIAL ANKLE JOINT AND PROSTHETIC DEVICES FORMED THEREWITH.

FIELD OF THE INVENTION

The present invention relates to a prosthetic device adapted for use on a lower extremity amputee. More particularly, the present invention is directed to an artificial ankle, and on a prosthetic leg device incorporating the ankle, that pivots to provide an amputee with an improved gait for running or walking. The present invention also enables a leg amputee to more easily ascend and descend staircases.

BACKGROUND OF THE INVENTION

Throughout modern human history, appropriate medical care sometimes has required amputation of a diseased or damaged limb. When a leg or portion thereof was amputated, often, the leg amputee was fitted with a prosthetic leg device so that the amputee could walk without the use of crutches or other aid devices. An early prosthetic leg device was simply a peg affixed to the remaining portion of the amputated leg of the amputee. Although effective, a "pegged" leg was not aesthetically pleasing.

Technological advancements of new materials enabled other types of prosthetic leg devices to be developed which were more aesthetically pleasing. Typically, these prosthetic leg devices included a calve portion, an ankle and a foot structure that simulated a human leg. Skillful fabrication of these prosthetic leg devices with advanced materials made them appear to be a real leg with a real foot structure. The advanced material which formed the anatomically-correct parts of the human body was either a plastic material or a rubber-like material having a color texture of human flesh. Now, a sock and footwear could be worn on the artificial foot to match the ones on the healthy foot so that the general public would be unable to visually determine that a person was an amputee.

Even though these new prosthetic devices appear generally life-like, several disadvantages remain. First, in order to assure proper balance,the lower leg portion below the "knee" is rearwardly offset from the upper leg portion above the "knee". Therefore, when simply standing, the artificial foot is positioned to the side of and behind the real foot, that is, in a staggered orientation, which presents an unnatural appearance. More importantly, though, none of these devices could perform functionally as well as a human leg. Unlike the function of a healthy human ankle, the typical ankle of the prosthetic leg device is a rigid, 90-degree connection unable to provide any pivotal movement between the calve portion of the leg and the foot structure. To use prior art prosthetic leg devices, the amputee is required to angularly swing his/her amputated leg in an arcuate motion relative to his/her healthy leg when making a step with the prosthesis. This arcuate motion, although unnatural, is necessary so that the prosthesis can be lifted above the walking surface to avoid being dragged when stepping. This arcuate motion adds stress to the healthy knee, leg and ankle of the amputee that could result in chronic pain and further injury. Thus, a tradeoff occurs. For a more aesthetically-pleasing prosthetic leg device, the amputee must suffer pain and/or risk future damage to his/her healthy leg.

A normal gait cycle of a human being includes three general phases which are dorsiflexion, plantarflexion and "push-off". Each of these phases is explained relative to an angular position, of the foot relative to a shin bone pivotally connected thereto by an ankle joint. The foot, of course, includes a heel disposed proximate to the ankle joint and a sole disposed distally to the ankle joint. The human foot is considered to be in a neutral position when it forms a 90-degree angle with the shin bone relative to a pivotal axis of the ankle joint. Dorsiflexion occurs when an acute angle is formed between the foot and the shin bone relative to the pivotal axis of the ankle joint. For example, dorsiflexion is best demonstrated during stepping as the heel on the foot of the advancing leg first contacts the walking surface immediately before the body weight of the amputee is transferred to the foot. Plantarflexion occurs when an obtuse angle is formed between the foot and the shin bone relative to the pivotal axis of the ankle joint. Plantarflexion is best demonstrated when the ankle of the advancing leg bends immediately after the heel contacts the walking surface so that both the heel and sole of the foot contact the walking surface in preparation of receiving the body weight of walking person. "Push-off" occurs as the trailing leg completes its step whereby the ankle joint becomes "locked" with the foot and shin bone in the neutral position so that the sole of the foot can propel the body weight of the walking person forward to transfer it onto the advanced leg.

Since prior art leg prosthetic devices are permanently fixed in the neutral position, effective "push off" occurs so that the amputee can complete his step and repeat his/her gait cycle. Unfortunately, none of the prior art prosthetic leg devices known to the present inventor provides dorsiflexion or plantarflexion. This lack of dorsiflexion and plantarflexion requires the amputee to swing the prosthetic leg outwardly in the arcuate fashion as described above when stepping. Furthermore, the lack of dorsiflexion and plantarflexion further hinders the amputee when ascending or descending stairs. With prior art prosthetic leg devices, an amputee is well advised to descend stairs one at a time by first lowering the prosthetic leg onto the next lower step before advancing the trailing healthy leg thereonto. Correspondingly, the amputee should ascend stairs one at a time by first raising the healthy leg on the step disposed immediately above before advancing the prosthetic leg thereon. It is extremely perilous for an amputee with a prosthetic leg to attempt to ascend or descend stairs by stepping on alternate steps with each leg. For example, descending stairs by an amputee with a prosthetic leg device in an alternating matter tends to thrust the amputee's body weight forward which could result in falling down the stairs. This thrusting effect is due to the absence of dorsiflexion.

Prior art prosthetic leg devices inhibit amputees from participating in various sporting events which require running. Not only is it difficult, if not impossible, to run in a prior art prosthetic leg device but also the rigidity of construction provides limited shock absorption capabilities. Much of the induced shock is absorbed by the body of the amputee that, in turns, causes further stress on the amputee's body. Such rigidity also results in minimal flexibility of the prosthetic leg device. Again, the amputee's body must compensate for this lack of flexibility.

There is a need in the marketplace to provide an artificial ankle joint that can be used with a prosthetic leg device so that a foot structure thereof can pivot about pivotal axis relative to a prosthetic leg portion. There is a further need in the marketplace to provide an artificial ankle joint for a prosthetic leg device which can execute the three general phases of dorsiflexion, plantarflexion and "push-off" to simulate a gait cycle of a normally healthy human being. It would be advantageous if this prosthetic leg device could be used for walking and running as well as ascending and descending stairs. It would be further advantageous if this prosthetic leg device could absorb shock and be flexible so as to relieve the amputee's body from absorbing shock and compensating for any lack of flexibility. There is a need to provide with such an ankle joint, and to provide a prosthetic leg device with such an ankle joint which prosthesis is lightweight. The present invention satisfies these needs and provides these advantages.

SUMMARY OF THE INVENTION

It is an object of the present invention to provide a new and useful artificial ankle joint for use with a prosthetic leg device having a foot structure and a proximal end portion so that the foot structure can pivot about a pivotal axis relative to the proximal end portion of the prosthetic leg device.

Another object of the present invention is to provide an artificial ankle for use with a prosthetic leg device which can execute the dorsiflexion, plantarflexion and "push-off" phases of a human gait cycle.

It is a further object of the present invention to provide an artificial ankle joint that can lock at a locking position so that the "push-off" phase of the human gait cycle can be executed.

It is yet another object of the present invention to provide an artificial ankle joint which automatically unlocks when the "push-off" phase of the gait cycle is completed.

A still further object of the present invention is to provide an artificial ankle joint which employs the body weight of the amputee to lock the artificial ankle joint at the locking position when executing the "push-off" phase of the gait cycle.

Yet another object of the present invention is to provide an artificial ankle joint which locks in the locking position only when a certain threshold of load is present.

Yet a still further object of the present invention is to provide an artificial ankle joint which can be disengaged from locking at the locking position regardless of the amount of load induced thereon.

Yet another object of the present invention is to provide an artificial ankle joint with a prosthetic leg device which can allow an amputee not only to walk and run similarly to a healthy human being but also ascend and descend stair cases like a healthy human being.

Still further, another object of the present invention is to provide an artificial ankle joint operative with a prosthetic leg device which is lightweight and aesthetically pleasing.

Another object of the present invention is to provide an artificial ankle joint that can absorb shock and can slightly flex in three dimensions.

According to the present invention, an artificial ankle joint and a prosthetic leg device incorporating such an artificial ankle joint is described for use on a human amputee. The prosthetic leg device has a proximal end portion and a foot structure, and the ankle joint is located between the proximal end portion and the foot structure. Broadly, the ankle joint includes a matable socket and head assembly interconnecting the proximal end portion and the foot structure for relative pivotal movement about a pivot axis between first and second pivot positions. The socket and head assembly includes a socket disposed on either the proximal end portion or the foot structure and a head disposed on the other. Preferably, the socket is disposed on the foot structure and the head is disposed on a distal end of a shaft that is secured to the proximal end portion. In any event, the head is sized to be matably received by the socket.

In order to assist the amputee during walking, a load sensitive locking mechanism is associated with the socket and head assembly. This locking mechanism is operative in response to a triggering compressive force between the socket and head in excess of a threshold magnitude to cause the socket and head assembly to lock at a selected locking position between the first and second pivot positions. When so locked, the locking mechanism prevents relative pivotal movement of the socket and head, but, in the absence of the triggering compressive force, the locking mechanism freely permits relative pivotal movement of the socket and head between the first and second positions.

Further, to assist the amputee in walking, the present invention provides a spring element associated with the socket and head assembly. This spring element resiliently biases this socket and head into the first pivot position. This first position corresponds to a dorsiflexion or "toes-up" position wherein the foot structure is oriented at an acute angle relative to the shin of the artificial prosthetic. The second rotational position of the socket and head assembly thus corresponds to a plantarflexion state wherein the foot structure is at an obtuse position. When in the locked position, the foot is at the neutral position generally at a 90-degree angle with respect to the shin of the artificial leg prosthetic. To further assist the amputee, it is preferred that the socket itself be received in a socket housing with a layer of stiff, yet resilient first material being interposed between the socket and the socket housing to imitate cartilage in the natural ankle joint. Moreover, the foot structure itself may be constructed of a stiff, yet resilient material to slightly flex during the walking motion, again to imitate the natural foot.

In its more detailed construction, the artificial prosthetic leg device of the present invention includes a prosthetic socket having a socket sized and adapted to releasably receive and retain the remaining residual limb portion of the amputated leg of the amputee. A shaft then extends along a central axis of the artificial leg, and the general region of the shin, and terminates in a head portion that forms one-half of the artificial ankle joint. The socket housing, the socket element and the first resilient material is then mounted on the foot structure opposite the toe portion thereof to define the other half of the artificial ankle joint. The socket includes an arcuate sidewall against which an outer peripheral surface of the head pivots. Here, the locking mechanism is preferably formed by a recess in the arcuate sidewall and a latch assembly carried by the head and shaft. When the triggering compressive force is present, the latch assembly then engages the recess at the selected locking position. The latch assembly preferably has a first rod slidably disposed in a bore formed axially through the shaft and has a latch element connected to a first end of the first rod. The latch element may be a rod-shaped member extending perpendicularly to the central axis. The first rod is resiliently biased to retain the latch element in a retracted state within a channel formed in the outer peripheral surface of the head parallel to the pivot axis so that, in the locked position, the latch element can move from the retracted state to an extended state thereby to engage the recess in the socket sidewall. The latch assembly may also include a second rod slidably disposed within the bore and extending outwardly therefrom opposite to the first rod. A first coil spring is operative to bias the first rod into the retracted state and a second coil spring is operative to resiliently retain, the first and second rods in spaced-apart relation from one another. The first coil spring has a spring constant that is preferably equal to-or greater than the spring constant of the second coil spring.

A restraining assembly may also be provided and associated with the locking mechanism. The restraining assembly operates in a restrained state to disable the locking mechanism so that the head and socket are permitted to pivot freely between the first and second positions while bypassing the locking position. In an unrestrained state, the locking mechanism is enabled. The restraining assembly in the exemplary embodiment includes an annular first collar connected to and extending around the shaft in stationary condition. An annular second collar is connected to the locking mechanism and is slidably received and rotatably mounted on the shaft. Each of the first and second collars have a plurality of alternating and longitudinally extending teeth and gaps therebetween. The teeth and gaps are sized so that respective ones of the teeth on each of the first and second collars will facially contact each other when the second collar is rotated into a first angular position to orient the restraining assembly in the restraining state. By virtue of the contact between the teeth, load forces are transferred away from the locking mechanism so that it is not subjected to the triggering compressive force. However, when the second collar is rotated to a second angular position to orient the restraining assembly in the unrestrained state, respective ones of the teeth on each of the first and second collars may slidably move into and out of respective ones of the gaps thereon thereby enabling the locking mechanism to receive the load and therefore the triggering compressive force. The restraining assembly may include a bushing slidably received in the shaft, a cap slidably received on the shaft and a retainer ring slidably disposed over the cap and releasably connected to the second collar so that the retainer ring and the second collar are rotatably connected to the cap and can rotate about the bushing and the shaft. The bushing can have a bushing channel formed in an outer peripheral bushing edge thereof. The second collar may include a set screw operably connected to the second collar through an outer peripheral collar edge. The set screw and bushing channel are operative to releasably retain the restraining assembly in the selected one of the retained and unretained states.

These and other objects of the present invention will become more readily appreciated and understood from a consideration of the following detailed description of the exemplary embodiments of the present invention when taken together with the accompanying drawings, in which:

BRIEF DESCRIPTION OF THE DRAWINGS

FIG. 4 is a side view in cross-section of a shaft of the artificial ankle joint of the present invention having a head portion connected to an end thereof and a load-sensitive locking mechanism disposed therewithin;

FIG. 5 is a side view in cross-section of a socket structure of the artificial ankle joint of the present invention showing a retainer member positioned above a socket disposed in a housing and secured thereinto by a stiff yet resilient rubber-like material;

FIG. 6 is an elevational side view partially broken away of the socket structure pivotally receiving and retaining the head portion of the shaft with a torsional spring resiliently biasing the shaft and the socket in a first pivot position;

FIG. 7 is an elevational side view partially broken away of the socket structure pivotally receiving and retaining the head portion of the shaft with the shaft and the socket in a second pivot position;

FIG. 8 is an elevational side view partially broken away of the socket structure pivotally receiving and retaining the head portion of the shaft with the shaft and the socket in a locking position disposed between the first and second pivot positions and the load-sensitive locking mechanism operative to permit relative pivotal movement of the shaft and the socket between the first and second pivot positions;

FIG. 9 is an elevational side view partially broken away of the socket structure pivotally receiving and retaining the head portion of the shaft with the shaft and the socket in the locking position and the load-sensitive locking mechanism operative to prevent relative pivotal movement of the shaft and the socket between the first and second pivot positions;

FIG. 10 is a side view in cross-section of a restraining assembly shown in an unrestrained state to enable the load-sensitive locking mechanism thereby preventing the shaft and the socket when in the locking position from relative pivotal movement therebetween;

FIG. 13 is a side view in elevation of the walking amputee with his/her prosthetic leg stepping forward whereby the heel and a sole thereof contact the walking surface with some body weight, i.e. load, being applied thereto so that a foot structure and a proximal end portion of the prosthetic leg device is naturally positioned in a plantarflexion phase of his/her gait;

FIG. 14 is an enlarged side view in elevation and partially broken away of a lower portion of the prosthetic leg device shown in FIG. 13 illustrating that the shaft and the socket structure are disposed in the second pivot position, that the restraining assembly is disposed in an unrestrained state with respective ones of plateaus partially engaged within and between respective ones of recesses and that a load, i.e. a load less than a predetermined threshold load, is being applied to the load-sensitive locking mechanism;

FIG. 15 is a side view in elevation of the walking amputee with his/her prosthetic leg trailing behind whereby the sole thereof contacts the walking surface with significant body weight, i.e. in excess of a predetermined threshold load, being applied thereto so that a foot structure and a proximal end portion of the prosthetic leg device is naturally positioned in the "push-off" phase of his/her gait;

FIG. 16 is an enlarged side view in elevation and partially broken away of a lower portion of the prosthetic leg device shown in FIG. 15 illustrating that the shaft and the socket structure are disposed in the locking position, that the restraining assembly is disposed in an unrestrained state with respective ones of plateaus completely engaged within and between respective ones of recesses and that load in excess of the predetermined threshold load is being applied to the load-sensitive locking mechanism thereby locking the same in the locking position;

FIG. 17 is a side view in elevation of the walking amputee descending a staircase with his/her prosthetic leg trailing behind on an upper step and his/her healthy leg securely placed on a lower step;

FIG. 18 is a side view in elevation of the walking amputee descending the staircase with his/her prosthetic leg securely placed on a subsequent lower step located immediately below the lower step shown in FIG. 17 and with his/her healthy leg trailing behind on the now upper step shown as the lower step in FIG. 17 to reflect descending the staircase in a fashion heretofore available to only non-amputees; and FIG. 19 is an enlarged side view in elevation and partially broken away of a lower portion of the prosthetic leg device shown in FIGS. 17 and 18.

DETAILED DESCRIPTION OF THE EXEMPLARY EMBODIMENTS

Figure 1:
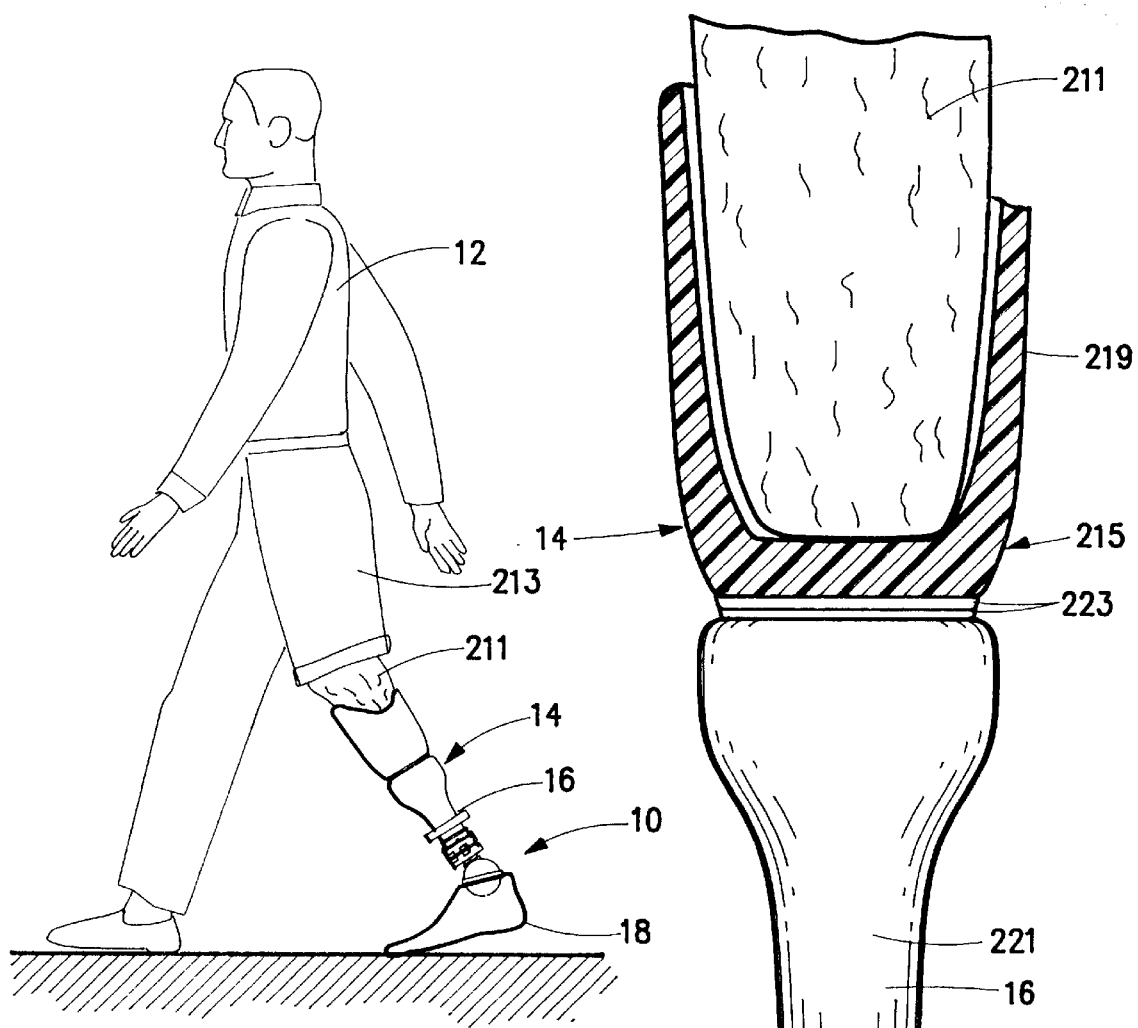
FIG. 1 is a side view in elevation of an amputee wearing a prosthetic leg device which employs an artificial ankle joint of the present invention.

An artificial ankle joint of the present invention which is adapted for use on a human amputee wearing a prosthetic leg device pivots so that the artificial ankle joint can better simulate the function of a human ankle. The artificial ankle of the present invention articulates between a dorsiflexion phase and a plantarflexion phase of a human's gait to simulate movement of a human's ankle. Furthermore, the artificial ankle joint provides "push-off", another critical phase of a human's gait, which is necessary to propel a human's body weight forward when transitioning body weight from the prosthetic leg to the healthy leg when stepping. Moreover, the artificial ankle of the present invention is operative so that an amputee can now descend and ascend stairs as a human with two healthy legs. An artificial ankle joint 10 is generally introduced in FIGS. 1–2. Here, artificial ankle joint 10 is adapted for use on a human amputee 12 wearing a prosthetic leg device 14 having a proximal end portion 16 and a foot structure 18. Artificial ankle joint 10 is disposed between proximal end portion 16 and foot structure 18.

Figure 3:
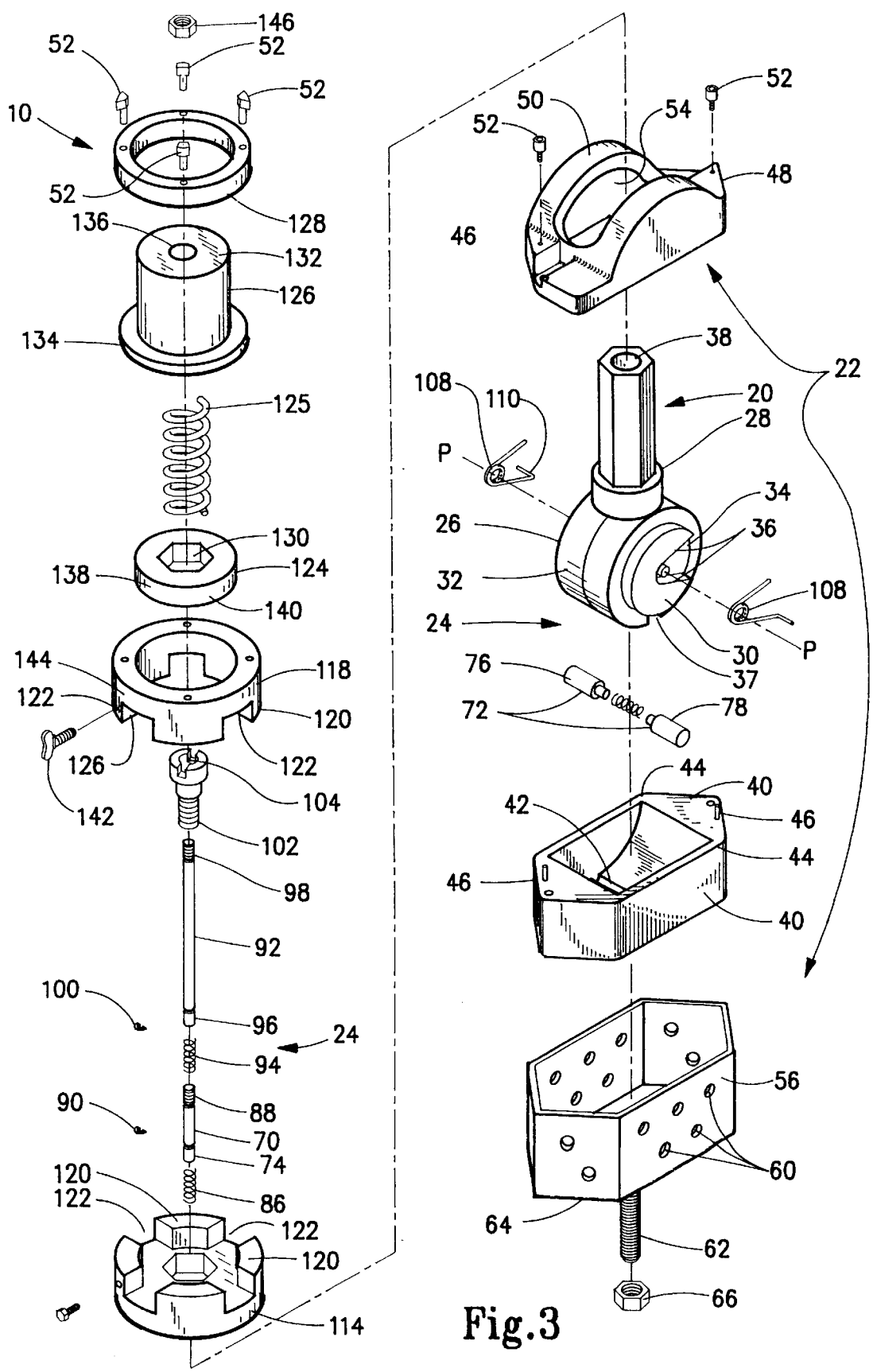
FIG. 3 is an exploded perspective view of the artificial ankle joint of the present invention shown in FIGS. 1 and 2.

With reference to FIGS. 3 and 4, ankle joint 10 includes a shaft 20 that has a hexagonal cross-sectional configuration and that extends along a central axis "C". Shaft 20 terminates in a distal head portion 26 disposed at end 28 of shaft 20. Head portion 26 has a pair of flat sides 30 and an outer peripheral edge surface 32 to define a generally cylindrical configuration. Each flat side has a shaft recess 34 formed thereinto, and a pair of oppositely projecting posts 36 extend centrally along a pivotal axis "P" from within a respective one of shaft recesses 34. An axial bore 38 extends longitudinally through shaft 20 along the central axis "C" to communicate with a transverse channel 39 formed into outer peripheral edge surface 32 of head portion 26. Channel 39 extends parallel to pivotal axis "P". Although not by way of limitation, shaft 20 is of a unitary construction and is fabricated from a rigid material such as plastic or metal.

In FIGS. 3, 5 and 6, it may be seen that socket structure 22 includes a socket member 40 sized and adapted to pivotally receive and retain head portion 26 of shaft 20. To this end, socket 40 has an arcuate sidewall 41 along which outer peripheral edge surface 32 pivots. Socket structure 22 and shaft 20 interconnect prosthetic leg device 14 and foot structure 18. Socket 40 has a detent, formed by a channel 42 described below, and a pair of notches 44 formed therein. A pair of guide pins 46 extend from socket 40 so that guide holes 48 formed in a socket cover 50 can receive guide pins 46 to assure proper alignment of socket cover 50 when releasably connected to socket 40 by a pair of fasteners 52 such as conventional screws having hex heads. An opening 54 formed into socket cover 50 is sized and adapted so that shaft 20 can pivot within socket 40 while retaining head portion 26 therein. Socket structure 22 includes a housing 56 sized and adapted to receive socket 40, and a stiff yet resilient first material 58 is interposed between housing 56 and socket 40. This material 58 is preferably an adhesive operative to resiliently retain socket 40 into housing 56. This first material may be such material as rubberized plastic or an equivalent. Furthermore, this stiff, yet resilient first material acts to absorb shock and to allow a slight flexing of artificial ankle joint 10 when in use, thus mimicking cartilage in the ankle joint. Housing 56 includes a plurality of holes 60 so that, when initially applied, the material 58 can flow into thereinto 56 to assure that housing 56 and stiff yet resilient adhesive material 58 adhere to each other. Housing 56 also includes a threaded rod 62 which extends from a bottom wall 64 thereof. A first threaded nut 66 is adapted to matably engage threaded rod 62.

With reference again to FIGS. 3–4, load-sensitive locking mechanism 24 is associated with socket 40 and head portion 26. Load-sensitive locking mechanism 24 includes a latch assembly 68 which cooperates with channel 42 formed in sidewall 41 of socket 40. Latch assembly 68 includes a first rod 70 slidably disposed in bore 38 of shaft 20 and a latch element 72 connected to a first end 74 of first rod 70 and oriented so that it extends perpendicularly to central axis "C". It is preferred that latch element 72 includes a first cylindrical piece 76 and a second cylindrical piece 78 which together form a crossbar on the distal end of rod 70. First cylindrical piece 76 includes an outer cylinder portion 80, and inner threaded portion 82 and shaft portion 84 disposed therebetween. Second cylindrical portion has a threaded axially-extending-hole sized and adapted to matably engage inner threaded portion 82 of first cylinder piece 76. Shaft portion 84 of first cylinder piece 76 is sized and adapted to be rotatably received by an eyelet 85 formed into first end 74 of first rod 70 so that latch element 72 can rotate thereabout when first and second cylindrical pieces 76 and 78 are matably connected together. First rod 70 is resiliently biased by a first coil spring 86. First coil spring 86 acts on first rod 70 in order to retain latch element 72 within a channel 39 of head portion 26 which is parallel to pivotal axis "P". A first continuous groove 88 formed into first rod 70 releasably receives a first spring clip 90 which secures first coil spring 86 around first rod 70 and within bore 38. Coil spring 86 compresses between spring clip 90 and a shoulder 89 located at a distal end of bore 38.

Latch assembly 68 also includes a second rod 92 slidably disposed in bore 38 and extending outwardly therefrom. One end of second rod 92 has a second continuous groove 96 formed thereinto and an opposite end threaded end 98. A second spring clip 100 is releasably received by second continuous groove 96, and a second coil spring 94 is, received on rod 92. After second coil spring 94 and second rod 92 are slidably disposed in bore 38, a threaded plug 102 having a plug hole 104 extending along the central axis "C" slides along second rod 92 and into bore 38 where threaded plug 102 matably engages a threaded inner wall portion 106 of shaft 20 which defines, in part, bore 38. Second coil spring 94 is positioned between first and second rods 70 and 92 respectively and engages first spring clip 90 so that it compresses between first spring clip 90 and second spring clip 100. Second coil spring 94 is operative to resiliently retain first rod 70 and second rod 92 in a spaced apart relationship from one another. First coil spring 70 has a first coil spring constant and second coil spring 94 has a second coil spring constant. The first coil spring constant is greater than the second coil spring constant so that latch element 72 can normally remain in a retracted state within channel 39 unless latch assembly 68 is otherwise acted upon by a load. When such a load is present, latch element is biased toward an extended state.

As best shown in FIGS. 3, and 6–9, a pair of spring elements 108 in a form of conventional torsional springs are associated with head 26 of shaft 20 and socket 40. Each spring element 108 is disposed with respective shaft recesses 34 formed into flat sides 30 of head portion 26 to surround respective posts 36. A spring end portion 110 of each spring element 108 is disposed and retained in respective notches 44 of socket 40.

Once shaft 20, socket 40, socket cover 50 and spring elements 108 are assembled in a manner as shown in FIGS. 6–9 into artificial ankle joint 10, one of ordinary skill in the art would appreciate that shaft 20 and socket 40 can pivotally move about pivotal axis "P" relative to each other between a first pivot position as shown in FIG. 6 and a second pivot position as shown in FIG. 7. A skilled artisan would further appreciate that spring elements 108 are operative to resiliently bias shaft 20 and socket 40 in the first pivot position (FIG. 6). A locking position is located between the first and second pivot positions as illustrated in both FIGS. 8 and 9. Specifically, the locking position is encountered when channel 39 of head portion 26 and detent 42 of socket 40 face each other.

As illustrated in FIG. 8, load-sensitive locking mechanism 24 is operative to permit relative pivotal movement of shaft 20 and socket 40 between the first and second pivotal positions thereby by-passing the locking position when a load "L" exerted upon locking mechanism 24 is less than a predetermined triggering threshold load. As illustrated in FIG. 9, load-sensitive locking mechanism 24 is operative to prevent relative pivotal movement of shaft 20 and socket 40 at the locking position when the triggering compressive load "L" exceeding the predetermined threshold load is exerted upon locking mechanism 24 as shaft 20 and socket 40 pivot relative to each other between the first and second pivot positions. When the triggering compressive force is present and when channels 39 and 42 register latch element 70 can move to the extended state thereby to engage channel 42. Therefore, in the locking position, detent channel 42 receives latch element 72 as it moves from channel 39. However, in the absence of registration of the channels 42 and 39, the compressive force compresses coil spring 94 such that its spring force loads against spring clip 88. When registration of channels 42 and 39 occurs, then, this spring force overcomes the spring 86 to cause latch element 72 to move to the extended state. It should be appreciated that load "L" is the fluctuating body weight of the amputee on the artificial ankle joint of the present invention as the amputee continuously transfers body weight from one leg to another while walking or running.

Figures 11, 12:
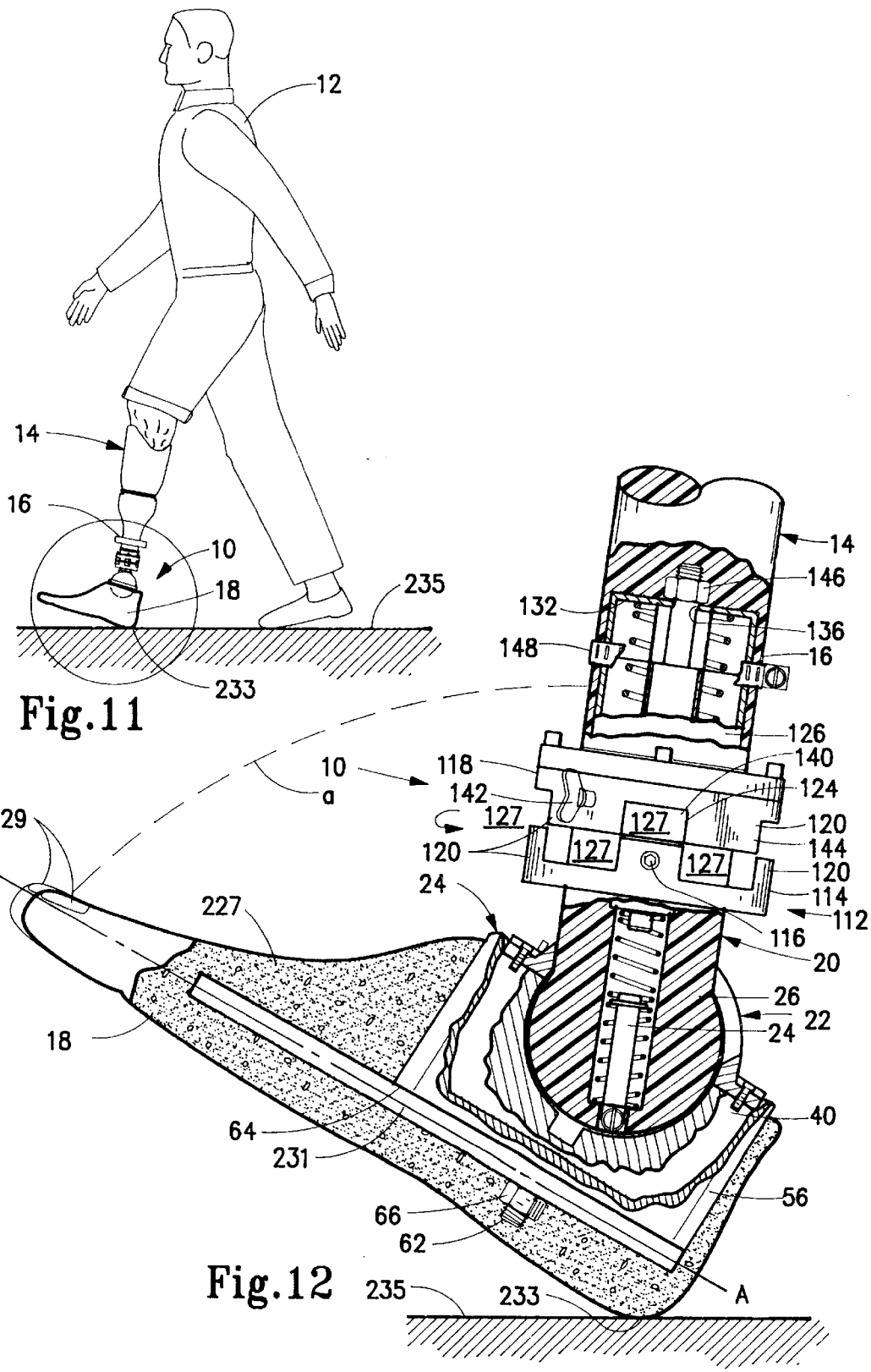
FIG. 11 is a side view in elevation of a walking amputee with his/her prosthetic leg stepping forward whereby a heel thereof contacts a walking surface with no body weight, i.e. load, being applied thereto so that a foot structure and a proximal end portion of the prosthetic leg device is naturally positioned in a dorsiflexion phase of his/her gait.
FIG. 12 is an enlarged side view in elevation and partially broken away of a lower portion of the prosthetic leg device shown in FIG. 11 illustrating that the shaft and the socket structure are disposed in the first pivot position, that the restraining assembly is disposed in an unrestrained state and that no load is being applied to the load-sensitive locking mechanism.

As best shown in FIGS. 3, 10, 12, 14, 16 and 19, artificial ankle joint 10 includes a restraining assembly 112 which is associated with locking mechanism 24 and is operative in a restrained state as shown in FIG. 19 and an unrestrained state as shown in FIGS. 12, 14 and 16. In the restrained state, the load is transferred away from locking mechanism 24 thereby disabling locking mechanism so that shaft 20 and socket 40 are permitted to pivot between the first and second pivot positions while by-passing the locking position. In the unrestrained state, locking mechanism 24 is enabled to receive the load thereby preventing shaft 20 and socket 40 in the locked position to pivot between the first and second pivot positions when the load on the locking mechanism exceeds the predetermined threshold load.

Restraining assembly 112 in the exemplary embodiment includes an annular first collar 114 is connected to and about shaft 20 in a stationary condition. A collar fastener 116 such as a hex-head bolt connects first collar at a select location along shaft 20 in the stationary condition. An annular second collar 118 is connected to locking mechanism 24 and is slidably received by and rotatably mounted onto shaft 20. Each of first and second collars 114 and 118 has a plurality of alternating, longitudinally extending teeth 120 and corresponding gaps 122 sized and adapted in a manner whereby, when second collar 118 is rotated into a first angular position as shown in FIG. 19 to orient restraining assembly 112 in the restraining state, respective ones of teeth 120 on each first and second collars 114 and 118 facially contact-each other thereby transferring the load away from locking mechanism 24. When second collar 118 is rotated to a second angular position different from said first angular position as shown in FIGS. 12, 14 and 16 to orient restraining assembly 112 in the unrestrained state, respective ones of teeth 120 on each first and second collars 114 and 118 can slidably move into and out of respective ones of gaps 122 of each first and second collars 114 and 118 thereby enabling locking mechanism 24 to receive the load.

As best shown in FIGS. 3, 10, 12, 14, 16 and 19, restraining assembly 112 also includes a bushing 124, a hollow cap 126 and a retainer ring 128. Bushing 124 is slidably received onto shaft 20 through a hexagonally-shaped bushing opening 130 (FIG. 3) formed axially therethrough which is sized and adapted to prevent rotational movement of bushing 124 about shaft 20. Cap 126 is generally cylindrical in shape and has a hexagonally-shaped hollowed interior 127 which is sized and adapted to slidably receive shaft 20 yet prevent rotational movement about shaft 20. Cap 126 also has a flat top 132 disposed at one end and a flange 134 extending radially outwardly at an opposite other end. A cap hole 136 extends axially through flat top 132. Retainer ring 128 is slidably disposed over cap 126 and is releasably connected to second collar 118 by a plurality of fasteners 52 in a manner so that retainer ring 128 and second collar 118 are rotatably connected to cap 126 and can rotate about bushing 124 and shaft 20. A coil spring 125 is disposed in the interior of cap 126 between top 132 and plug 102.

With reference to FIGS. 3, 10 and 19, bushing 124 includes a bushing channel 138 formed in an outer peripheral bushing edge 140 thereof and second collar 118 includes a set screw 142 operably connected to second collar 118 through an outer peripheral collar edge 144. Set screw 142 and bushing channel 138 are operative to releasably retain restraining assembly 112 in one of the restrained state and the unrestrained state. As shown in FIGS. 12, 14, 16 and 19, retaining assembly 112 is operably connected to latch assembly 68 by a second threaded nut 146 matably engaged with threaded end 98 of second rod 92 extending through cap hole 136. Retainer assembly 112 is then connected to proximal end portion 14 of prosthetic leg device 14 whereby proximal end portion 14 slidably receives cap 126. A conventional hose clamp 148 is tightened to grip both proximal end portion 14 and retainer assembly 112.

Figure 2:
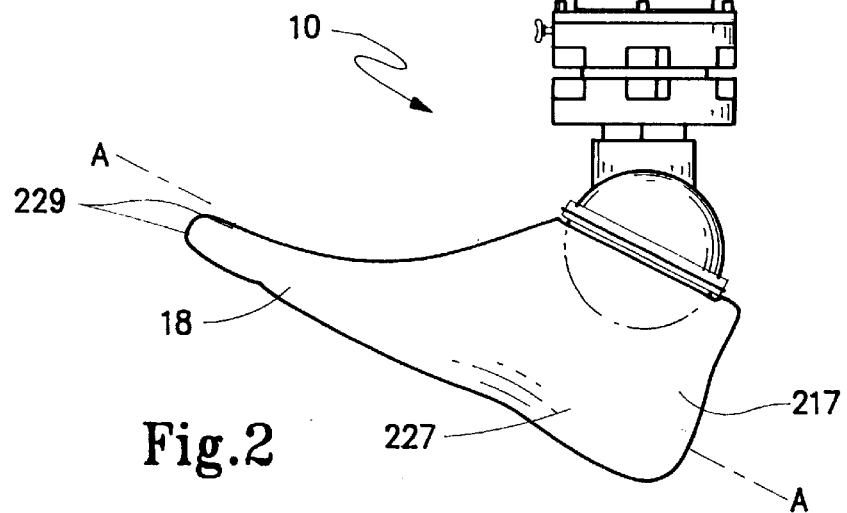
FIG. 2 is an enlarged side view in elevation of the prosthetic leg device employing the artificial ankle joint of the present invention as shown in FIG. 1 with a prosthetic socket partially broken away that releasably receives and retains a remaining residual limb portion of an amputated leg.

It should be clearly understood that the above-described construction of the restraining assembly 112 is merely provided for illustrative purposes. Numerous other assemblies can readily be designed by the skilled mechanic to selectively enable and disable the load-sensitive locking mechanism. Indeed, even the load-sensitive locking mechanism could be modified by the skilled artisan to a different structure that would equivalently perform the desired selective locking of the pivoting ankle joint without departing from the inventive concepts described herein In any event, the artificial ankle joint of the present invention can either be retrofitted onto prior art prosthetic leg devices having proximal end portion and a foot structure or it can be fabricated with a new and improved prosthetic leg device considered to be a second exemplary embodiment of the present invention. As best shown in FIGS. 1 and 2, prosthetic leg device 14 of the exemplary embodiment of the present invention incorporates artificial ankle joint 10 as described above and is adapted for use on a human amputee 12 having a residual limb leg portion 211 remaining on an amputated leg 213 of amputee 12. Prosthetic leg device 14 includes a prosthetic socket 215 and a foot structure 18. Prosthetic socket 215 has a socket 219 which is sized and adapted to releasably receive and retain the remaining residual limb portion 211. Prosthetic socket 215 includes a stubshaft 221 which interconnects socket 219 and shaft 20. When appropriate, one or more shims 223 can be disposed between socket 219 and stubshaft 221 to adjust prosthetic leg device 14 to suit the height of amputee 12. A rigid second retainer ring 225 is slidably received by proximal end portion 16 of prosthetic leg device 14 to provide extra rigidity proximate to the connection between proximal end portion 16 and artificial ankle joint 10.

Foot structure 18 includes socket 40 and housing 56. Housing 56 is connected to the foot structure 18 of prosthetic leg device 14. Foot structure 18 includes an artificial foot 227 which extends along a longitudinal axis "A" and is connected to housing 56. Artificial foot 227 is fabricated from a stiff yet resilient material such as rubber or plastic and has a plurality of artificial toes extending longitudinally therefrom along a longitudinal axis "A". Artificial foot 227 and disposed proximally from said socket. Foot structure 18 also includes a support plate 231 which is connected to bottom wall 64 of housing 56 by first threaded nut 66 matably engaged with threaded rod 62. It is preferred that artificial foot 227 be molded to and around housing 56 and support plate 231.

Operation of artificial ankle joint 10 of the present invention as well as prosthetic leg device 14 incorporating artificial ankle joint 10 is best shown in FIGS. 11–19. In FIGS. 11 and 12, walking amputee steps forward with his/her prosthetic leg device 14. A heel 233 of artificial foot 227 contacts a walking surface 235 with no body weight, i.e. load, being applied thereto. Artificial foot 227 of foot structure 18 is disposed at an acute angle "a" relative to shaft 20 when in the first pivot position to render the plurality of toes 229 in a toes-up condition. This toes-up condition is typically referred to as dorsiflexion of a human's gait. Foot structure 18 and proximal end portion 16 of the prosthetic leg device 14 is now naturally positioned in the dorsiflexion phase of his/her gait. In FIG. 12 wherein prosthetic leg device 14 is shown in the dorsiflexion phase, shaft 20 and socket structure 22 are resiliently biased and disposed in the first pivot position. Restraining assembly 112 is disposed in the unrestrained state. Additionally, no load is being applied to load-sensitive locking mechanism 24 since neither of the first and second coil springs 86 or 94 is compressed.

In FIGS. 13 and 14, walking amputee 12 with his/her prosthetic leg device 14 steps forward and heel 233 and a sole 237 of artificial foot 227 contact walking surface 235 with some body weight, i.e. load, being applied thereto. Artificial foot 227 of foot structure 18 and proximal end portion 16 of prosthetic leg device 14 is naturally positioned in a plantarflexion phase of the amputee's gait. Artificial foot 227 of foot structure 18 is at an obtuse angle "b" relative to shaft 20 when in the second pivot position to render said plurality of toes in a toes-down condition. The toes-down condition is typically referred to as plantarflexion of a human's gait. Foot structure 18 and proximal end portion 16 of the prosthetic leg device 14 is now naturally positioned in the plantarflexion phase of his/her gait. In FIG. 14, shaft 20 and the socket structure 22 are disposed in the second pivot position. Restraining assembly 112 is disposed in the unrestrained state with respective ones of plateaus 120 partially engaged within and between respective ones of recesses 122. Some load less than a predetermined threshold load, is being applied to load-sensitive locking mechanism. This load compresses spring 125, and first and second coil springs 86 and 94 are somewhat compressed.

In FIGS. 15 and 16, walking amputee 12 has his/her prosthetic leg device 14 trailing behind while advancing healthy leg 239. Sole 237 of artificial foot 227 contacts walking surface 235 with significant body weight, i.e. in excess of a predetermined triggering threshold load, being applied thereto so that artificial foot 227 of foot structure 18 and proximal end portion 16 of prosthetic leg device 14 is naturally positioned in the "push-off" phase of his/her gait which substantially perpendicular to shaft 20 when in the locked position. "Push-off" enables amputee 12 to propel his/her body weight forward to initiate the next step in the gait.

In FIG. 16, shaft 20 and socket structure 22 are disposed in the locking position which is desirable when "push-off" is required. Restraining assembly 112 is disposed in an unrestrained state with respective ones of teeth 120 completely engaged within and between respective ones of gaps 122. A load in excess of the predetermined threshold load is being applied to load-sensitive locking mechanism 24 thereby causing the same to lock in the locking position when in the course of pivoting the channels 39 and 42 have registered whereby latch element 72 has extended into the extended and locked state. Note first and second coil springs 86 and 94 are as fully compressed as they can be. Here also, foot structure 18 can slightly flex which, along with compression of the material 58 mimics the natural foot when "locked" by muscles for push-off. The restorative force of spring 125 further provides push-off as the amputee transfers weight to the forward foot. After push-off is complete and the compressive forces removed, springs 108 cause foot structure 18 to pivot to the dorsiflexion (toes-up) position so that the prosthetic leg can move forward to take amputee to swing the prosthetic in a lateral arc.

In FIGS. 17–19, walking amputee 12 is descending a staircase 241. In FIG. 17, prosthetic leg device 14 trails behind on an upper step 243 and his/her healthy leg 239 is securely placed on a lower step 245. In FIG. 18, walking amputee 12 continues to descend staircase 241 with his/her prosthetic leg device securely placed on a subsequent lower step 247 located immediately below lower step 245 and with his/her healthy leg trailing behind on lower step 245. Descending staircase 241 in a fashion described above has never been heretofore available to amputees, at least without risk of grave danger. In FIG. 19, shaft 20 and socket structure 22 can pivotally move relative to each other between the first and second pivotal positions regardless if the load exceeds the threshold load because restraining assembly 112 is disposed in the restrained state with respective ones of teeth 120 on first collar 114 contact respective ones of the teeth 120 on second collar 118 thereby preventing operation, i.e. linear displacement, of locking mechanism 24.

As a result, the present invention can pivot between the first position and the second position and can execute the dorsiflexion, plantarflexion and "push-off" phases of a human gait cycle. Similar to a real human ankle, the artificial ankle joint of the present invention can lock at the locking position so that the "push-off" phase of the human gait cycle can be executed and can automatically unlock when the "push-off" phase of the gait cycle is completed. The body weight of the amputee is employed to lock at the locking position when executing the "push-off" phase of the gait cycle as well as to unlock when the "push-off" phase of the gait cycle is completed. The artificial ankle joint locks in the locking position only when a certain threshold of load is sensed. The artificial ankle joint can be disengaged from locking at the locking position when the restraining assembly is in the restraining state regardless of the amount of load induced on the locking mechanism. The artificial ankle joint allows an amputee not only to walk similarly to a healthy human being but also ascend and descend stair cases like a healthy human being. The artificial ankle joint with a prosthetic leg device is lightweight and aesthetically pleasing. Lastly, the artificial ankle joint can absorb shock and can flex in three dimensions as a result of the stiff yet resilient adhesive material that retains the socket in the housing.

Accordingly, the present invention has been described with some degree of particularity directed to the exemplary embodiments of the present invention. It should be appreciated, though, that the present invention is defined by the following claims construed in light of the prior art so that modifications or changes may be made to these embodiments of the present invention without departing from the inventive concepts contained herein.

I claim:

1. In a prosthetic leg device adapted to be worn by a human amputee wherein said leg device has a proximal end portion adapted to be secured to the amputee and a distal foot structure, the improvement comprising a pivoting ankle joint disposed between said proximal end portion and said foot structure, said ankle joint including a matable socket and head assembly that includes a shaft secured to said proximal end portion and extending along a central axis to terminate in said head, said matable socket and head assembly interconnecting said proximal end portion and said foot structure for relative pivotal movement about a pivot axis between a first pivot position wherein said foot structure is oriented at an acute angle with respect to the central axis and a second pivot position wherein said foot structure is oriented at an obtuse angle with respect to the central axis, said socket and head assembly including a socket disposed on one of said proximal end portion and said foot structure and a head sized to be matably received by said socket and disposed on another of said proximal end portion and said foot structure, said pivoting ankle joint further including a load-sensitive locking mechanism associated with said socket and head assembly, said locking mechanism operative in response to a triggering compressive force between said socket and head in excess of a threshold magnitude to cause said socket and head assembly to lock at a selected locking position between the first and second pivot positions corresponding to said foot structure being oriented substantially perpendicular to the central axis, thereby to prevent relative pivotal movement of said socket and head and operative in an absence of a triggering compressive force to permit relative pivotal movement of said socket and head between the first and second positions, and including a spring element associated with said socket and head assembly and operative to resiliently bias said socket and head assembly into the first pivot position.

2. The improvement according to claim 1 including a socket housing disposed on said foot structure, said socket housing being sized and adapted to mount said socket and including a stiff yet resilient first material interposed between said socket and said socket housing.

3. The improvement according to claim 2 wherein said foot structure is constructed of a stiff yet resilient second material.

4. The improvement according to claim 1 wherein said socket is secured to said foot structure.

5. The improvement according to claim 4 wherein said socket has an arcuate sidewall along which an outer peripheral surface of said head pivots, said locking mechanism including a recess formed in said arcuate sidewall and a latch assembly carried by said head, said latch assembly operative in response to the triggering compressive force to engage the recess at the selected locking position.

6. The improvement according to claim 5 wherein said latch assembly includes at least a first rod slidably disposed in a bore formed axially through said shaft and a latch element connected to a first end of said first rod and extending perpendicularly to the central axis, said first rod being resiliently biased to retain said latch element in a retracted state within a channel formed into the outer peripheral surface of said head portion parallel to said pivotal axis so that in the locked position said latch element can move from the retracted state to an extended state thereby to engage said recess.

7. The improvement according to claim 6 wherein said latch assembly includes a second rod slidably disposed within said bore and extending outwardly therefrom opposite said first rod, a first coil spring operative to bias said first rod into the retracted state and a second coil spring operative to resiliently retain said first and second rods in a spaced apart relationship from one another.

8. The improvement according to claim 7 wherein said first coil spring has a first coil spring constant and wherein said second coil spring has a second coil spring constant, said first coil spring constant being equal to or greater than said second coil spring constant.

9. The improvement according to claim 1 including a restraining assembly associated said locking mechanism and operative in a restrained state to disable said locking mechanism so that said head and said socket are permitted to pivot between the first and second pivot positions while by-passing the locking position and in an unrestrained state to enable said locking mechanism.

10. In a prosthetic leg device adapted to be worn by a human amputee wherein said leg device has a proximal end portion adapted to be secured to the amputee and a distal foot structure, the improvement comprising a pivoting ankle joint disposed between said proximal end portion and said foot structure, said ankle joint including a matable socket and head assembly interconnecting said proximal end portion and said foot structure for relative pivotal movement about a pivot axis between first and second pivot positions, said socket and head assembly including a socket disposed on one of said proximal end portion and said foot structure and a head sized to be matably received by said socket and disposed on another of said proximal end portion and said foot structure, said pivoting ankle joint further including a load-sensitive locking mechanism associated with said socket and aid head assembly, said locking mechanism operative in response to a triggering compressive force between said socket and head in excess of a threshold magnitude to cause said socket and head assembly to lock at a selected locking position between the first and second pivot positions thereby to prevent relative pivotal movement of said socket and head and operative in an absence of a triggering compressive force to permit relative pivotal movement of said socket and head between the first and second positions, further including a restraining assembly associated with said locking mechanism and operative in a restrained state to disable said locking mechanism so that said head and said socket are permitted to pivot between the first and second pivot positions while by-passing the locking position and in an unrestrained state to enable said locking mechanism, said restraining assembly including an annular first collar connected to and about said shaft in a stationary condition and an annular second collar connected to said locking mechanism and slideably received by and rotatably mounted onto said shaft, each of said first and second collars having a plurality of alternating longitudinally extending teeth and gaps sized so that when said second collar is rotated into a first angular position to orient said restraining assembly in the restrained state, respective ones of said teeth on each of said first and second collars facially contact each other thereby transferring load forces away from said locking mechanism, and when said second collar is rotated to a second angular position different from said first angular position to orient said restraining assembly in the unrestrained state, respective ones of said teeth on each of said first and second collars slideably move into and out of respective ones of said gaps of said first and second collars thereby enabling said locking mechanism to receive the load.

11. The improvement according to claim 10 wherein said restraining assembly includes a bushing slidably received onto said shaft, a cap slidably received onto said shaft and a retainer ring slidably disposed over said cap and releasably connected to said second collar in a manner so that said retainer ring and said second collar are rotatably connected to said cap and can rotate about said bushing and said shaft.

12. The improvement according to claim 11 wherein said bushing includes a bushing channel formed in an outer peripheral bushing edge thereof and wherein said second collar includes a set screw operably connected to said second collar through an outer peripheral collar edge, said set screw and said bushing channel operative to releasably retain said restraining assembly in one of the restrained state and the unrestrained state.

13. A prosthetic leg device with an artificial ankle joint adapted for use on a human amputee having a residual limb leg portion remaining on an amputated leg of the amputee, comprising:

(a) a prosthetic socket having a socket sized and adapted to releasably receive and retain the remaining residual limb portion of the amputated leg of the amputee;

(b) a shaft extending along a central axis and having a first end portion connected to said prosthetic socket and a head portion disposed opposite of said first end portion;

(c) a foot structure including a socket having an arcuate sidewall, said socket sized and adapted to pivotally receive and retain said head portion of said shaft along an outer peripheral surface of said head portion, whereby said shaft and said socket can pivotally move about a pivotal axis relative to each other between a first pivot position and a second pivot position; and (d) a load-sensitive locking mechanism associated with said socket and said head portion and operative to prevent relative pivotal movement of said shaft and said socket at a locking position located between the first and second pivot positions when a triggering load exceeding a predetermined threshold load is exerted upon said locking mechanism as said shaft and said socket pivot relative to each other between the first and second pivot positions and to permit relative pivotal movement of said shaft and said socket between the first and second pivotal positions thereby by-passing the locking position when a load is exerted upon said locking mechanism that is less than the triggering load, said locking mechanism including a recess formed in said arcuate sidewall and a latch assembly carried by said head, said latch assembly operative in response to the triggering compressive force to engage the recess at the selected locking position.

14. A prosthetic leg device according to claim 13 including a spring element interconnecting said head portion of said shaft and said socket and operative to resiliently bias said shaft and said socket in the first pivot position.

15. A prosthetic leg device according to claim 13 wherein said foot structure includes a housing sized and adapted to receive said socket and a stiff, yet resilient first material disposed between said socket and said housing and operative to resiliently retain said socket into said housing.

16. A prosthetic leg device according to claim 13 wherein said foot structure includes an artificial foot extending along a longitudinal axis, said artificial foot fabricated from a stiff, yet resilient second material and having a distal toe portion extending longitudinally therefrom and disposed in spaced-relation from said socket.

17. A prosthetic leg device according to claim 16 wherein said artificial foot is disposed at an acute angle relative to said shaft when in the first pivot position to render said toe portion in a toes-up condition, at an obtuse angle relative to said shaft when in the second pivot position to render said toe portion in a toes-down condition and substantially perpendicular to said shaft when in the locked position.

18. A prosthetic leg device according to claim 13 including a restraining assembly associated said locking mechanism and operative in a restrained state to disable said locking mechanism so that said shaft and said socket are permitted to pivot between the first and second pivot positions while by-passing the locking position and in an unrestrained state to enable said locking mechanism.

19. A prosthetic leg device according to claim 13 wherein said prosthetic socket includes a stubshaft interconnecting said socket and said shaft.

* * * * *